(12) United States Patent
Nallani et al.

(10) Patent No.: US 11,241,494 B2
(45) Date of Patent: *Feb. 8, 2022

(54) METHOD FOR ELICITING AN IMMUNE RESPONSE TO AN IMMUNOGEN

(71) Applicant: AGENCY FOR SCIENCE, TECHNOLOGY AND RESEARCH, Singapore (SG)

(72) Inventors: Madhavan Nallani, Singapore (SG); Fabien Decaillot, Singapore (SG); Zhikang Fu, Singapore (SG); Xingfang Su, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,232

(22) Filed: Mar. 28, 2018

(65) Prior Publication Data

US 2018/0214540 A1 Aug. 2, 2018

Related U.S. Application Data

(63) Continuation of application No. 14/646,008, filed as application No. PCT/SG2013/000478 on Nov. 11, 2013, now Pat. No. 9,962,438.

(30) Foreign Application Priority Data

Nov. 19, 2012 (SG) ............................ 201208483-6

(51) Int. Cl.
| | |
|---|---|
| A61K 39/385 | (2006.01) |
| A61K 47/34 | (2017.01) |
| A61K 9/127 | (2006.01) |
| A61K 9/00 | (2006.01) |
| A61K 39/12 | (2006.01) |
| A61K 39/00 | (2006.01) |

(52) U.S. Cl.
CPC .......... *A61K 39/385* (2013.01); *A61K 9/0019* (2013.01); *A61K 9/1273* (2013.01); *A61K 39/12* (2013.01); *A61K 47/34* (2013.01); *A61K 2039/55566* (2013.01); *A61K 2039/6093* (2013.01); *C12N 2760/16134* (2013.01)

(58) Field of Classification Search
CPC .... A61K 39/385; A61K 9/1273; A61K 47/34; A61K 2039/6093
USPC ..................................................... 530/387.1
See application file for complete search history.

(56) References Cited

U.S. PATENT DOCUMENTS

| 7,217,427 | B2 | 5/2007 | Discher et al. | |
|---|---|---|---|---|
| 7,867,512 | B2 | 1/2011 | Discher et al. | |
| 8,378,003 | B2 * | 2/2013 | Manish | B01D 69/144 |
| | | | | 522/88 |
| 9,962,438 | B2 * | 5/2018 | Nallani | A61K 9/1273 |
| 10,364,350 | B2 * | 7/2019 | Nallani | C08L 9/00 |
| 2008/0311045 | A1 * | 12/2008 | Hardy | A61K 9/5146 |
| | | | | 424/9.3 |
| 2011/0046074 | A1 * | 2/2011 | Kumar | B01D 71/78 |
| | | | | 514/21.2 |
| 2012/0129270 | A1 * | 5/2012 | Nallani | C08L 71/02 |
| | | | | 436/501 |
| 2013/0239339 | A1 | 9/2013 | Bown et al. | |
| 2013/0316008 | A1 | 11/2013 | Nallani et al. | |
| 2015/0174250 | A1 | 6/2015 | Griffiths et al. | |
| 2019/0322864 | A1 * | 10/2019 | Nallani | C08L 15/00 |
| 2021/0251899 | A1 * | 8/2021 | Nallani | A61K 39/39 |

FOREIGN PATENT DOCUMENTS

| CN | 101005827 A | 7/2007 |
|---|---|---|
| CN | 102770477 A | 11/2012 |
| GN | 101854917 A | 10/2010 |
| WO | WO 2005/016259 A2 | 2/2005 |
| WO | WO 2010/123462 A1 | 10/2010 |
| WO | WO 2011/109512 A1 | 9/2011 |
| WO | WO 2012/018306 A1 | 2/2012 |
| WO | WO 2016/055611 A | 4/2016 |

OTHER PUBLICATIONS

Luo et al. (Am Chem Soc. Aug. 17, 2016; 138(32): 10157-10162).*
Avsar etal (Frontiers in Chemistry 6: 1-29 (Jan. 8, 2019)).*
PCT Notification of Transmittal of the International Search Report and the Written Opinion of the International Searching Authority, or the Declaration for PCT Counterpart Application No. PCT/SG2013/000478, 8 pgs., (Feb. 3, 2014).
Christophe Barnier Quer, et al., "Polymersomes Enhance the Immunogenicity of Influenza Subunit Vaccine", Polymer Chemistry, vol. 2, pp. 1482-1485, (2011).
Evan A. Scott, et al., "Dendritic Cell Activation and T Ceil Priming with Adjuvant- and Antigen-Loaded Oxidation-Sensitive Polymersomes", Biomaterials, vol. 33, pp. 6211-6219, (2012).
PCT Notification Concerning Transmittal of International Preliminary Report on Patentability (Chapter I of the Patent Cooperation Treaty) for PCT Counterpart Application No. PCT/SG2013/000478, 5 pgs., (May 28, 2015).
European Patent Office Communication enclosing Extended European Search Report for corresponding European Patent Application No. 13855088.4, 9 pp., (Jul. 18, 2016).
Madhavan Nallani, et al., "Proteopolymersomes: In Vitro Production of a Membrane Protein in Polymersome Membranes", Biointerphases, vol. 6, No. 4, pp. 153-157, (Dec. 2011).

(Continued)

*Primary Examiner* — Lynn A Bristol
(74) *Attorney, Agent, or Firm* — Womble Bond Dickinson (US) LLP

(57) ABSTRACT

The invention relates to methods for eliciting an immune response to an immunogen, and in particular, to such methods using polymersomes as carriers for immunogen.

4 Claims, 5 Drawing Sheets

(56) References Cited

OTHER PUBLICATIONS

Caterina Lopresti, et al., "Polymersomes: Nature Inspired Nanometer Sized Compartments", Journal of Materials Chemistry, vol. 19, No. 22, pp. 3576-3590, (2009).
First Office Action issued by the State Intellectual Property Office of China (SIPO) for corresponding Chinese Patent Application No. 201380070982.5. 14 pp. (including English translation), (Nov. 2, 2016).
Dian R. Arifin, et al., "Polymersome Encapsulated Hemoglobin: A Novel Type of Oxygen Carrier," Biomacromolecules, vol. 56, pp. 2171-2182 (2005).
Sylvia May, et al., "In Vitro Expressed GPCR Inserted in Polymersome Membranes for Ligand-Binding Studies," Agnew. Chem. Int. Ed., vol. 52, pp. 749-753 (2013).
Douglas L. Gettel, et al., "Mixing, Diffusion, and Percolation in Binary Supported Membranes Containing Mixtures of Lipids and Amphiphilic Block Copolymers," J. Am. Chem. Soc., vol. 136, pp. 10186-10189 (2014).
Ahmed, Fariyal, et al., "Polymersomes as Viral Capsid Mimics", Drug Development Research 67, (2006), 4-14.
Ahmed, Fariyal, et al., "Shrinkage of a Rapidly Growing Tumor by Drug-Loaded Polymersomes: pH-Triggered Release through Copolymer Degradation", Molecular Pharmaceutics vol. 3, No. 3, (Mar. 18, 2006), 340-350.
De Hoog, Hans-Peter M., et al., "Conformational Antibody Binding to a Native, Cell-Free Expressed GPCR in Block Copolymer Membranes", Plos One vol. 9, Issue 10, (Oct. 2014), 1-7.
Fu, Zhikang, et al., "Multicompartmentalized polymersomes for selective encapsulation of biomacromolecules", Chem. Commun. vol. 47, (2011), 2862-2864.
Li, Shuliang, et al., "Self-Assembled Poly(butadiene)-b-Poly(ethylene oxide) Polymersomes as Paclitaxel Carriers", Biotechnol Prog. 23(1), (2007), 278-285.

Rajagopal, Karthikan, et al., "Polymersomes and Wormlike Micelles Made Fluorescent by Direct Modifications of Block Copolymer Amphiphiles", International Journal of Polymer Science, vol. 2010, (2010), 1-10.
(IPOS) Intellectual Property Office of Singapore, Search Report for counterpart Singapore Application No. 10201704135Q, 3 pgs. (Feb. 12, 2018).
(IPOS) Intellectual Property Office of Singapore, Written Opinion for counterpart Singapore Application No. 10201704135Q, 7 pgs. (Feb. 12, 2018).
N.A. Christian, et al.,"Tat-Functionalized Near-Infrared Emissive Polymersomes for Dendritic Cell Labeling," Bioconjugate Chem., vol. 18, No. 1, pp. 31-40 (Nov. 22, 2006).
Examination Report for counterpart EP Application No. 13858088.4, 6 pgs. (Sep. 5, 2018).
Jung Seok Lee, et al., "Polymersomes for drug deliver: Design, formation and characterization," Journal of Controlled Release, vol. 161, No. 2, pp. 473-483 (Jul. 20, 2012).
"*Staphylococcus aureus* alpha toxin" Wikipedia entry last edited on Feb. 10, 2021, retrieved from <https://en.wikipedia.org/w/index.php?title=Staphylococcus_aureus_alpha_toxin&oldid=1006014637>.
"*Staphylococcus aureus* alpha toxin" Wikipedia entry last edited on Aug. 29, 2012, retrieved from <https://en.wikipedia.org/w/index.php?title=Staphylococcus_aureus_alpha_toxin&oldid=509711145>.
Song et al., "Structure of Staphylococcal x-Hemolysin, a Heptameric Transmembrane Pore", Science, vol. 274, Dec. 13, 1996, pp. 1859-1866.
First Office Action for Chinese Application No. 202010019429.0, dated Sep. 3, 2021, 10 pages.
First Search Document for Chinese Application No. 202010019429.0, dated Aug. 27, 2021, 1 page.

* cited by examiner

METHOD FOR ELICITING AN IMMUNE RESPONSE TO AN IMMUNOGEN

CROSS-REFERENCE TO RELATED APPLICATION

This patent application is a continuation of U.S. patent application Ser. No. 14/646,008, filed May 19, 2015, which is a U.S. National Phase Application under 35 U.S.C. § 371 of International Application No. PCT/SG2013/000478, filed Nov. 11, 2013, entitled METHOD FOR ELICITING AN IMMUNE RESPONSE TO AN IMMUNOGEN, which claims the benefit of priority of Singapore Patent Application No. 201208483-6, filed Nov. 19, 2012, the contents of which were incorporated by reference in their entirety for all purposes.

TECHNICAL FIELD

The invention relates to methods for eliciting an immune response to an immunogen, and in particular, to such methods using polymersomes as carriers for the immunogen.

BACKGROUND

Although immunization is a well-established process, there are differences in the response level elicited between different immunogens antigens (used interchangably herein). Of interest, membrane proteins form a class of antigens that produce a low response level, which in turn means that a large number of membrane proteins are required in order to generate or elicit an immune response to the desired level. Membrane proteins are notoriously difficult to synthesize and are insoluble in water without the presence of a detergent. This makes it expensive and difficult to obtain membrane proteins in sufficient quantity for the purpose of immunization.

Furthermore, membrane proteins require proper folding in order to function correctly. The immunogenicity of correctly folded membrane proteins are much better than solubilized membrane proteins, which are not folded in a physiologically relevant manner. Thus, even though adjuvants may be used to boost the immunogenicity of such solubilized membrane proteins, it is an inefficient method that does not provide too much of an advantage.

In addition, the common procedure to raise antibodies against membrane proteins often require a prior knowledge of their native structure within membranes in order to design suitable epitopes that can be used for the immunization. This immunization is usually performed independently using isolated peptides which could adopt conformations very differently from the one occurring in the full protein in its native membrane habitat. Hence, there is a high risk that the antibodies raised by the isolated peptides may not recognize the target protein in vivo after all.

Although transfected cells and lipid-based systems have been used to present membrane protein antigens to increase the chances of isolating antibodies that may efficient in vivo, these systems are often unstable, tedious and costly. Moreover, the current state of the art for such membrane protein antigens is to use inactive virus-like particles for immunization.

Therefore, there remains a need to provide for alternative methods that overcome, or at least alleviate, the above problems.

SUMMARY

The invention described herein provides a method to present membrane proteins to evoke immune response without addition of known adjuvants using proteopolymersomes. The present inventors have surprisingly found that by providing the circumferential membrane of a polymersome to allow membrane proton antigens to properly fold, a stronger immune response than free membrane proteins antigens is evoked. Consequently, an increase in the efficiency of antibody production in a subject, such as a mammalian animal, is achieved. The increase in the efficiency can be attained with or without the use of adjuvants. Because full-length and properly folded membrane protein antigens are presented, the antibodies produced by using the invention described herein would also have a higher affinity for in vivo membrane protein targets and may able to neutralize the virus if the antibodies are raised virus antigens.

Thus, in accordance with one aspect of the invention, it is disclosed a method for eliciting in a subject an immune response to an immunogen. The method may include injecting the subject with a composition including a polymersome carrier having a circumferential membrane of an amphiphilic polymer. The composition further includes an immunogen integrated into the circumferential membrane of the amphiphilic polymer of the polymersome carrier. The immunogen may be a membrane-associated protein or lipid antigen.

In another aspect of the invention, there is provided a composition for intradermal, intraperitoneal, subcutaneous, intravenous, or intramuscular injection, or non-invasive administration of an immunogen. The composition may include a polymersome carrier having a circumferential membrane of an amphiphilic polymer. The composition may further include an immunogen integrated into the circumferential membrane of the amphiphilic polymer of the polymersome carrier. The immunogen may be a membrane-associated protein or lipid antigen. The composition may be used in antibody discovery, vaccine discovery, or targeted delivery.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1:
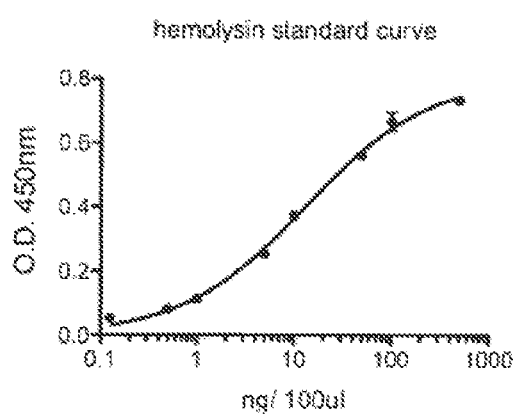
FIG. 1 shows a standard curve of alpha-hemolysin concentration.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

In the present context, polymersomes are vesicles with a polymeric membrane, which are typically, but not necessarily always, formed from the self-assembly of dilute solutions of amphiphilic block copolymers, which can be of different types such as diblock and triblock (A-B-A or A-B-C). Polymersomes may also be formed of tetrablock pentablock copolymers. For triblock copolymers, the central block is often shielded from the environment by its flanking blocks, while diblock copolymers self-assemble into bilayers, placing; two hydrophobic blocks tail-to-tail, much to the same effect. In most cases, the vesicular membrane has an insoluble middle layer and soluble outer layers. The driving force for polymersome formation by self-assembly is considered to be the microphase separation of the insoluble blocks, which tend to associate in order to shield themselves from contact with water. Polymersomes possess remarkable properties due to the large molecular weight of the constitutent copolymers. Vesicle formation is favored upon an increase in total molecular weight of the block copolymers. As a consequence, diffusion of the (polymeric) amphiphiles in these vesicles is very low compared to vesicles formed by lipids and surfactants. Owing to this less mobility of polymer chains aggregated in vesicle structure, it is possible to obtain stable polymersome morphologies. Unless expressly stated otherwise, the term "polymersome" and "vesicle", as used hereinafter, are taken to be analogous and may be used interchangably.

In the present context, an antigen is any substance that may be specifically bound by components of the immune system and only antigens that are capable of eliciting (or evoking or inducing) an immune response are said to be immunogenic and are called immunogens. Membrane proteins form a class of antigens that produce a low response level. Of specific interest, membrane-associated proteins (i.e. the antigens mentioned herein) are integrated (or incorporated or carried) into the wall of a polymersome, allowing the membrane-associated proteins to be folded in a physiologically relevant manner (i.e. presently termed as polymersome carrier or antigen-presenting polymersome, both terms used interchangably hereinafter). This greatly boosts the immunogenicity of the membrane proteins so that when compared to free membrane proteins, a smaller amount of membrane proteins can be used to produce the same level of immune response. Furthermore, the larger size of the polymersomes (compared to free membrane proteins) allows them to be detected by the immune system more easily.

Since the immunization is performed using the full protein (instead of fragment thereof) in a synthetic environment that allows its proper folding, the probability of isolating antibodies that are capable of detecting the membrane protein in vivo would be higher. Moreover, the immunization and antibody generation can be performed without any prior knowledge of the membrane protein structure, which is otherwise necessary when using a peptide-based immunization approach.

Further, when compared to other techniques, present approach allows rapid and cost effective production of membrane protein inserted in a stable membrane environment.

Thus, in accordance with one aspect of the present invention, a method for eliciting in a subject an immune response to an immunogen is disclosed. The method may include injecting the subject with a composition including polymersome carrier having a circumferential membrane of an amphiphilic polymer. The composition further includes an immunogen integrated into the circumferential membrane of the amphiphilic polymer of the polymersome carrier. The immunogen is a membrane-associated protein. Alternatively, the immunogen may also be a lipid antigen. In such embodiments, the immunogen may be a synthetic lipid or a natural lipid.

The frequency of the injection may be determined and adjusted by a person skilled in the art, dependent on the level of response desired. For example, weekly or bi-weekly injections of the polymersome carriers may be given to the subject, which may include a mammalian animal. The immune response can be measured by quantifying the blood concentration level of antibodies in the mammalian animal against the initial amount of immunogens carried by the polymersome carrier. The structure of the polymersomes may include amphiphilic block copolymers self-assembled into a vesicular format and integrated membrane proteins spanning the wall of the vesicles, whereby the membrane proteins are the antigens to be presented, and are incorporated by method of reconstitution or in vitro synthesis or spontaneous insertion. The membrane proteins can be reconstituted with the aid of detergents, surfactants, temperature change or PH change. The vesicular structure provided by the amphiphilic block copolymers allows the membrane protein antigens to be folded in a physiologically correct and functional manner, allowing the immune system of the target mammalian animal to detect said antigens, thereby producing a strong immune response.

In various embodiments the injection of the composition may include intraperitoneal, subcutaneous, or intravenous, intramuscular injection, or non-invasive administration.

In alternative embodiments, the injection of the composition may include intradermal injection. It has been surprisingly found by the inventors in experiments involving intradermally injected mice that alpha-hemolysin presenting polymersomes are much more efficient than free alpha-hemolysin in eliciting immune response, where the alpha-hemolysin presenting polymersomes elicited a higher immune response than free alpha-hemolysin in the $2^{nd}$ and $3^{rd}$ bleed (see Examples section below).

The immune response level may be further heightened or boosted by including an adjuvant in the composition including the polymersome carrier carrying the immunogen. In such embodiments, the polymersome earlier carrying the immunogen and the adjuvant are administered simultaneously to the subject.

In alternative embodiments, the adjuvant may be administered separately from the administration of the composition including the polymersome carrier carrying the immunogen. The adjuvant may be administered before, simultaneously, or after the administration of the composition including the polymersome carrier carrying the immunogen. For example, the adjuvant may be injected to the subject after injecting the composition including the polymersome carrier carrying the immunogen.

A person skilled in the art would readily recognize and appreciate that the types of adjuvant to be injected depend on the types of immunogen to be injected. The immunogen may be an antigen of bacterial, viral or fungi origin. For example, in the case where the antigen is alpha-hemolysin, the adjuvant may be complete Freund adjuvant. Other antigen-adjuvant pairs are also suitable for use in the present method. In certain embodiments, the use of adjuvants is not needed. In yet certain embodiments, the present method works better, i.e. stronger immune response being evoked, without the use of adjuvants.

In other embodiments, the membrane-associated protein may be a transmembrane protein, G protein-coupled receptor, neurotransmitter receptor kinase, porin, ABC transporter, ion transporter, acetylcholine receptor and cell adhesion receptor. The membrane proteins may also be coupled with a tag or may be tag-free. If the membrane proteins are tagged, then the tag may be selected from epitopes such as VSV, His tag, Strep tag, Flag tag, Intein tag or GST tag or a partner of a high affinity binding pair such as biotin avidin or from a label such as a fluorescent label, an enzyme label, NMR label or isotope label.

The membrane proteins is may be presented prior to incorporation, or incorporated simultaneously with the production of the protein through a cell-free expression system. The cell-free expression system may be an in vitro transcription and translation system.

The cell-free expression system may also be an eukaryotic cell-free expression system such as the TNT® system based on rabbit reticulocytes, wheat germ extract or insect extract, a prokaryotic cell-free expression system or an archaic cell-free expression system.

As mentioned above, the polymersomes may be formed of amphiphilic diblock or triblock copolymers. In various embodiments, the amphiphilic polymer may include at least one monomer unit of a carboxylic acid, an amide, an amine, an alkylene, a dialkylsiloxane, an ether or an alkylene sulphide.

In certain embodiments, the amphiphilic polymer may be a polyether block selected from the group consisting of an oligo(oxyethylene) block, a poly(oxyethylene) block, an oligo(oxypropylene) block, a poly(oxypropylene) block, an oligo(oxybutylene) block and a poly(oxybutylene) block. Further examples of blocks that may be included in the polymer include, but are not limited to, poly(acrylic acid), poly(methyl acrylate), polystyrene, poly(butadiene), poly(2-methyloxazoline), poly(dimethyl siloxane), poly(e-caprolactone), poly(propylene sulphide), poly(N-isoproylacrylamide), poly(2-vinylpyridine) poly(2-(diethylamino)ethyl methacrylate), poly(2-(diisopropylamino)ethylmethacrylate), poly(2-(methacryloyloxy)ethylphosphorylcholine) and poly(lactic acid). Examples of a suitable amphiphilic polymer include, but are not limited to, poly(ethyl ethylene)-b-poly(ethylene oxide) (PEE-b-PEO), poly(butadiene)-b-poly(ethylene oxide) (PBD-b-PEO), poly(styrene)-b-poly(acrylic acid) (PS-PAA), poly(2-methyloxazoline)-b-poly(di-methylsiloxane)-b-poly(2-methyloxazoline) (PMOXA-b-PDMS-b-PMOXA), poly(2-methyloxa-zoline)-b-poly(dimethylsiloxane)-b-poly(ethylene oxide) (PMOXA-b-PDMS-b-PEO), poly(ethylene oxide)-b-poly(propylene sulfide)-b-poly(ethylene oxide) (PEO-b-PPS-b-PEO) and a poly(ethylene oxide)-b-poly(buylene oxide) block copolymer. A block copolymer can be further specified by the average block length of the respective blocks included in a copolymer. Thus $PB_M PEO_N$ indicates the presence of polybutadiene blocks (PB) with a length of M and polyethyleneoxide (PEO) blocks with a length of N, M and N are independently selected integers, which may for example be selected in the range from about 6 to about 60. Thus $PB_{35}PEO_{18}$ indicates the presence of polybutadiene blocks with an average length of 35 and of polyethyleneoxide blocks with an average length of 18. In certain embodiments, the PB-PEO diblock copolymer comprises 5-50 blocks PB and 5-50 blocks PEO. Likewise, $PB_{10}PEO_{24}$ indicates the presence of polybutadiene blocks with an average length of 10 and of polyethyleneoxide blocks with an average length of 24. As a further example $E_O B_P$ indicates the presence of ethylene blocks (E) with a length of O and butylene blocks (B) with a length of P, O and P are independently selected integers, e.g. in the range from about 10 to about 120. Thus $E_{16}B_{22}$ indicates the presence of ethylene blocks with an average length of 16 and of butylene blocks with an average length of 22.

In certain embodiments, the polymersome carrier may contain one or more compartments (or otherwise termed "multicompartments"). Compartmentalization of the vesicular structure of polymersome allows for the co-existence of complex reaction pathways in living cell and helps to provide a spatial and temporal separation of many activities inside a cell. Accordingly, more than one type of immunogen may be incorporated in the polymersome carrier. The different immunogens may have the same or different isoforms. Each compartment may also be formed of a same or a different amphiphilic polymer. In various embodiments, two or more different immunogens are integrated into the circumferential membrane of the amphiphilic polymer. Each compartment may encapsulate at least one of peptide, protein, and nucleic acid. The peptide, protein, or nucleic acid may be immunogenic.

In the case where the polymersome carrier contains more than one compartment, the compartments may comprise an outer block copolymer vesicle and at least one inner block copolymer vesicle, wherein the at least one inner block copolymer vesicle is encapsulated inside the outer block copolymer vesicle. In some embodiments, each of the block copolymer of the outer vesicle and the inner vesicle includes a polyether block such as a poly(oxyethylene) block, a poly(oxypropylene) block, and a poly(oxybutylene) block. Further examples of blocks that may be included in the copolymer include, but are not limited to, poly(acrylic acid), poly(methyl acrylate), polystyrene, poly(butadiene), poly(2-methyloxazoline), poly(dimethyl siloxane), poly(L-isocyanoalanine(2-thiophen-3-yl-ethyl)amide), poly(e-caprolactone), poly(propylene sulphide), poly(N-iscpropylacrylamide), poly(2-vinylpyridine), poly(2-(diethylamino)ethyl methacrylate), poly(2-

(diisopropylamino)ethylmethacrylate), poly(2-(methacryloyloxy)ethylphosphorylcholine) and poly(lactic acid). Examples of suitable outer vesicles and inner vesicles include, but are not limited to, poly(ethyl ethylene)-b-poly(ethylene oxide) (PEE-b-PEO), poly(butadiene)-b-poly(ethylene oxide) (PBD-b-PEO), poly(styrene)-b-poly(acrylic acid) (PS-b-PAA), poly(ethylene oxide)-poly(caprolactone) (PEO-b-PCL), poly(ethylene oxide)-poly(lactic acid) (PEO-b-PLA), poly(isoprene)-poly(ethylene oxide) (PI-b-PEO), poly(2-vinylpyridine)-poly(ethylene oxide) (P2VP-b-PEO), poly(ethylene oxide)-poly(N-isopropylacrylamide) (PEO-b-PNIPAm), poly(ethylene glycol)-poly(propylene sulfide) (PEG-b-PPS), poly(methylphenylsilane)-poly(ethylene oxide) (PMPS-b-PEO-b-PMPS-b-PEO-b-PMPS), poly(2-methyloxazoline)-b-poly-(dimethylsilaxane)-b-poly(2-methyloxazoline) (PMOXA-b-PDMS-b-PMOXA), poly(2-methyloxa-zoline)-b-poly(dimethylsiloxane)-b-poly(ethylene oxide) (PMOXA-b-PDMS-b-PEO), poly[styrene-b-poly(L-isocyanoalanine(2-thiophen-3-yl-ethyl)amide] (PS-b-PIAT), poly(ethylene oxide)-b-poly(propylene sulfide)-b-poly(ethylene oxide) (PEO-b-PPS-b-PEO) and a poly(ethylene oxide)-poly(buylene oxide) (PEO-b-PBO) block copolymer. A block copolymer can be further specified by the average number of the respective blocks included in a copolymer. Thus $PS_M$-$PIAT_N$ indicates the presence of polystyrene blocks (PS) with M repeating units and poly(L-isocyanoalanine(2-thiophen-3-yl-ethyl)amide) (PIAT) blocks with N repeating units. M and N are independently selected integers, which may for example be selected in the range from about 5 to about 95. Thus $PS_{40}$-$PIAT_{50}$ indicates the presence of PS blocks with an average of 40 repeating units and of PIAT blocks with an average of 50 repeating units.

By "encapsulated" it is meant that the inner vesicle is completely contained inside the outer vesicle and in surrounded by the vesicular membrane of the outer vesicle. The confined space surrounded by the vesicular membrane of the outer vesicle forms one compartment. The confined space surrounded by the vesicular membrane of the inner vesicle forms another compartment.

Further details of suitable multicompartmentalized polymersomes can be found in PCT Publication No. WO 2012/018306, the contents of which being hereby incorporated by reference in its entirety bar all purposes.

The polymersomes may also be free-standing or immobilized on a surface, such as those described in PCT Publication No. WO 2010/123462, the contents of which being hereby incorporated by reference in its entirety for all purposes.

In additional embodiments, a secondary protein that complexes with the membrane protein antigen may be encapsulated or incorporated in the lumen of the polymersome carrier. Advantageously, the secondary protein stabilises the membrane protein antigen in a specific conformation.

In another aspect of the invention, there is provided a composition for intradermal intraperitoneal, subcutaneous, intravenous, or intramuscular injection, or non-invasive adminstration of an immunogen. The composition may include a polymersome carrier having a circumferential membrane of an amphiphilic polymer. The composition may further include an immunogen integrated into the circumferential membrane of the amphiphilic polymer of the polymersome carrier. The immunogen may be a membrane-associated protein or lipid antigen. The composition may be used in antibody discovery, vaccine discovery, or targeted delivery.

In summary, the present invention demonstrates for the first time the use of membrane proteins incorporated within polymersomes to generate an immune response. Although a combination of polymersomes and membrane protein antigens have been used to elicit an immune response previously, the polymersomes were used with known adjuvant molecules, and the membrane proteins were not presented in a physiologically relevant manner. On the other hand, the present polymersome carriers are not used as an adjuvant; rather the polymersome carriers are used as vehicles to accommodate the membrane protein antigens, thereby allowing proper folding of the membrane protein antigens therein, which consequently enables a better immune response to be evoked than conventional detergent solubilized membrane protein antigens.

Compared to existing techniques, present invention offers the following advantages:

The immune response could possibly be further boosted by using adjuvants.

the polymers are inherently robust, and can be tailored or functionalized to increase their circulation time in the body.

The polymers are cheap and quick to synthesize.

The amount of membrane proteins required to elicit an immune response is lesser.

The full length of membrane protein antigen is used, making it more likely that the antibodies generated will be able to detect membrane proteins in vivo The membrane proteins can be incorporated into polymersome carriers via in vitro translation or transcription which is advantageous to raise antibodies against difficult membrane protein antigens.

With these advantages, the invention described herein provides a method to evoke an immune response from membrane protein antigens that is faster, cheaper, more accurate, and simpler than current state of the art. Possible applications of present invention include production of antibodies in vaccination and generating therapeutic antibodies.

In order that the invention may be readily understood and put into practical effect, particular embodiments will now be described by way of the following non-limiting examples.

EXAMPLES

Example 1

A method for eliciting in mice an immune response to alpha-hemolysin using alpha-hemolysin-presenting polymersomes is now described in the following paragraphs.

Materials & Methods

Poly(butadiene-b-ethylene oxide) ($PBd_{21}$-$PEO_{14}$) BD21 amphiphilic block copolymer was purchased from Polymer Source (Canada). Alpha-hemolysin from *staphylococcus aureus*, 3-(N-morpholino) propanesulfonic acid (MOPS), Tris(hydroxymethyl)aminomethane hydrochloride (Tris), magnesium chloride and sodium chloride were all bought from Sigma Aldrich (Singapore), Tetrahydrofuran (THF) was purchased from Tedia (Ohio, USA).

Preparation of Polymersomes

The polymersomes were prepared by film rehydration method. BD21 polymer was dissolved in THF, and dried as a thin film on the wall of a conical bottom glass tube under a stream of nitrogen gas. The polymer film is further dried under vacuum. Subsequently, ultrapure water was added to the tube and stilled to rehydrate the film and allow spontaneous formation of polymer vesicles, resulting in a uniformly turbid solution. The resulting vesicle dispersion was then extruded with 0.45 μm PVDF filters (Millipore), and dialysis against ultrapure water was carried out to remove any remaining solvent. Alpha-hemolysin was dissolved in MOPS-NaCl buffer (0.01M MOPS, 0.1M NaCl, pH 7).

The polymersomes were formed by adding an aliquot of alpha-hemolysin solution to polymer vesicle dispersion. The mixture was then incubated to allow reconstitution of alpha-hemolysin into the polymersomes. Subsequently, free alpha-hemolysin was separated from alpha-hemolysin-presenting polymersomes using centrifugal filters. The alpha-hemolysin-presenting polymersomes were then resuspended in 50 ul of TMN buffer (100 mM Tris, 50 mM $MgCl_2$ and 100 mM NaCl, adjusted to pH 7.5).

Quantification of Alpha-Hemolysin Concentration

The quantification of the amount of alpha-hemolysin inserted into alpha-hemolysin-presenting polymerosomes was determined using a standard curve obtained from known concentrations of free hemolysin (FIG. 1). 100 ng/well of polyclonal anti-alpha-hemolysin antibodies in coating buffer (0.1M $CO_3/HCO_3$ pH9-9.8) were coated in a 96-well plate overnight at 4° C. The day after, the wells were blocked in blocking buffer (1% BSA in 1X PBS) at room temperature (RT) for 1 h. Different concentrations free alpha-hemolysin starting from 500 ng/100 ul in blocking buffer were then incubated for 1 h, RT. Additionally, alpha-hemolysin-presenting polymersome samples were prepared in the same buffer (1:10 dilution) and incubated similarly. Subsequently, anti-alpha-hemolysin mouse serum (1:1000) in blocking buffer was applied, followed by anti-mouse HRP-coupled antibodies (1:4000). Peroxidase activity was quantified through triplicate measurements with TMB substrate. Triplicate measurements were also performed on non-alpha-hemolysin-coated wells to determine non-specific binding (NSB). Extrapolation using the obtained standard curve allowed us to estimate the amount of inserted alpha-hemolysin proteopolymerosomes to be 1.32 μg/ml+/−0.6 (n=4).

Injection of Polymersomes 100-150 ng per mouse of alpha-hemolysin-presenting proteopolymersomes were injected intraperitoneally or intradermally in C57B/6 mice (3 mice per group) as follows: $1^{st}$ boost on day 1, $2^{nd}$ boost on day 14 followed by a boost every 7 days for 4 more weeks. Blood samples were collected before each immunization using capillaries sampling from the mice's cheek.

Quantification of Immune Response 100 ng per well of free alpha-hemolysin in boating buffer were coated in a 96-well plate overnight. The wells were blocked using blocking buffer the day after. Each blood sample was diluted (1:100 or 1:1000) in blocking buffer and incubated on alpha-hemolysin-coated or non-coated wells for 1 h at RT. After 3 washes (PBS 1X), anti-mouse HRP-coupled antibodies (1:4000) were incubated for 1 h at RT followed by 3 washes and TMB substrate reaction.

Results & Discussion

To demonstrate the present method of using, membrane protein antigen-presenting polymersomes to elicit an immune response, alpha-hemolysin (antigen) was incorporated into BD22 polymersomes to form alpha-hemolysin presenting polymersomes.

Figure 2A:
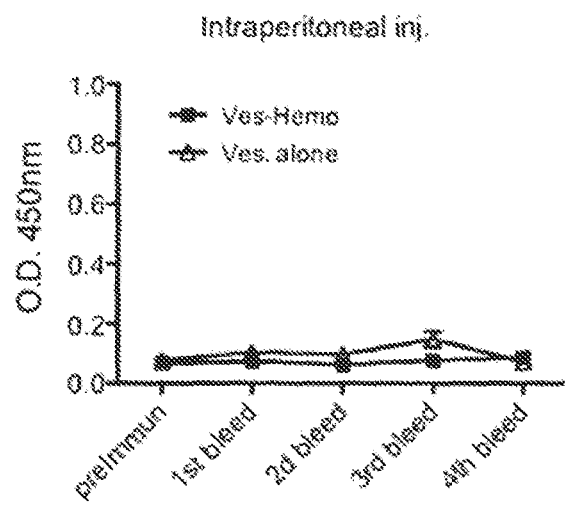
FIG. 2A shows optical density measurements of antibody titers O.D., measurements using alpha-hemolysin-coated plate. 3 mice were injected with alpha-hemolysin-presenting polymersomes (closed squares labeled "Ves-Hemo") while 3 other mice received empty polymersomes (open triangles labeled "Ves. alone") Sera were diluted (1:1000) and anti-mouse HRP-coupled antibody was used as a secondary antibody. An increasing anti-alpha-hemolysin titer was observed over time with repeated immunizations.
Figure 2B:
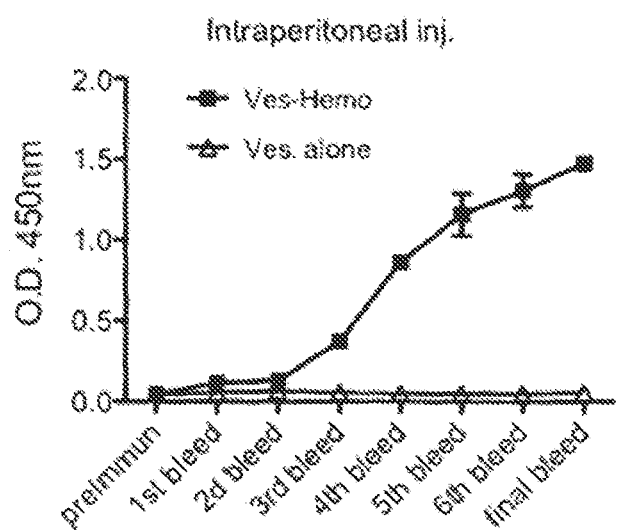
FIG. 2B shows the same experiment procedures as FIG. 2A using non-coated plates. No antibody binding is detected.

To demonstrate the immunogenicity of the alpha-hemolysin-presenting polymersomes, they were injected intraperitoneally into 3 mice while 3 other mice received polymersomes without proteins. The sera were tittered against an alpha-hemolysin-coated plate (FIG. 2A). A robust antibody titer was obtained after the $3^{rd}$ injection of alpha-hemolysin-presenting polymersomes while empty polymersomes remained without effect throughout the experiment. No titer was detected when the sera were tested on plates without alpha-hemolysin coating, showing that the antibody titer was specific for alpha-hemolysin (FIG. 2B). This shows that alpha-hemolysin presenting polymersomes are able to elicit an immune response, raising antibodies against alpha-hemolysin for immunization or antibody production, even though the amount of alpha-hemolysin used (100-150 ng) is much lower than the usual microgram dosage.

Figure 3:
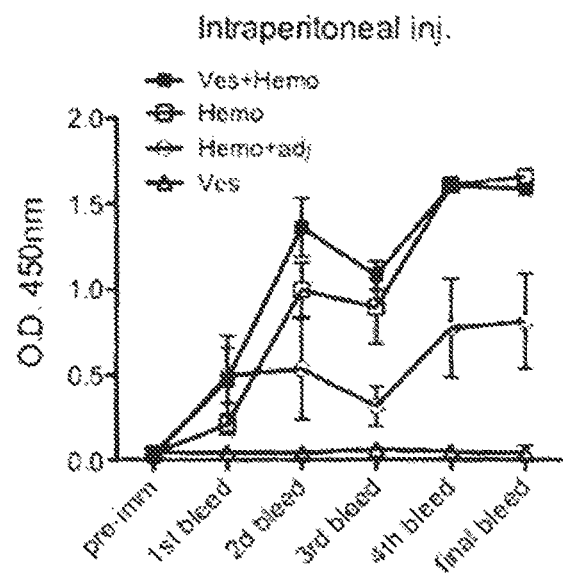
FIG. 3 shows optical density measurements of immune response. Alpha-hemolysin-presenting polymersomes (closed squares labeled "Ves+Hemo") gave a higher response than free alpha-hemolysin (open squares labeled "Hemo") up to the $3^{rd}$ bleed, after which a saturation of the immune response was achieved for both. Interestingly, alpha-hemolysin with adjuvant (open circles labeled "Hemo+adj") gave a lower immune response than freealpha-hemolysin. Empty polymersomes (open triangles labeled "Ves") remained non-immunogenic.

To further analyse the immunogenicity of alpha-hemolysin presenting polymersomes, the polymersomes were injected into 3 mice, while 9 other mice were injected with various controls (3 mice with TMN buffer, 3 mice with free alpha-hemolysin and 3 mice with alpha-hemolysin and complete Freund adjuvant), FIG. 3 shows the immunogenic response of the mice through 5 injections. As with the previous experiment, alpha-hemolysin presenting polymersomes were able to elicit an immune response. Surprisingly, free alpha-hemolysin of a comparable amount (100 ng) was also able to elicit an immune response without the use of adjuvants, although the response was somewhat lower for the first 3 injections. Free alpha-hemolsyin injected together with an adjuvant led to a less efficient response while empty polymersomes remained non-immunogenic. Hence, part of the observed immune response obtained using alpha-hemolysin presenting polymerosomes could be due to immunogenicity of alpha-hemolysin itself. Such immunogenicity without adjuvant was also observed in a study where a truncated version of alpha-hemolysin was used to immunize mice, although a much higher dosage was used (5 μg).

Figure 4:
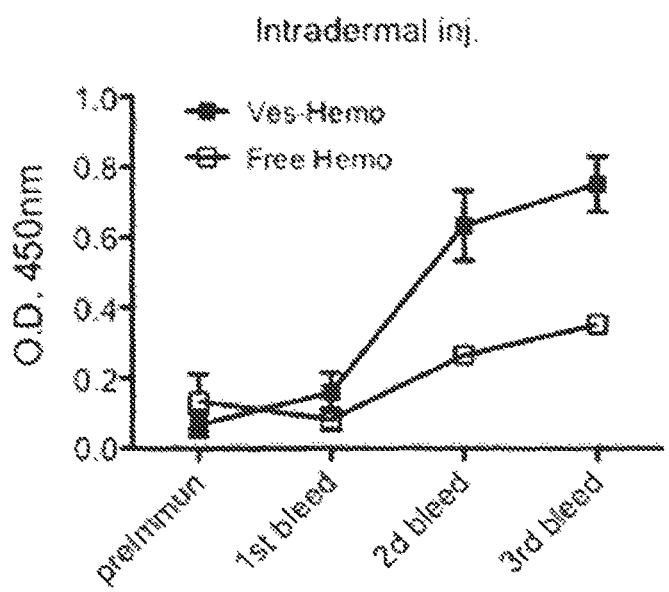
FIG. 4 shows optical density measurements of immune response. Alpha-hemolysin-presenting polymersomes (closed squares labeled "Ves-Hemo") elicited a higher immune response than free alpha-hemolysin (open squares labeled "Free Hemo") in both the $2^{nd}$ and $3^{rd}$ bleeds when intradermal injection is performed.
Figure 5:
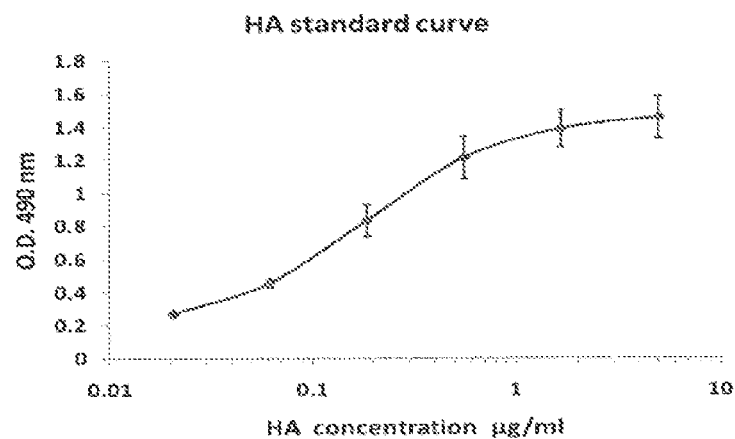
FIG. 5 shows a standard curve of hemagglutinin (HA) concentration.
Figure 6:
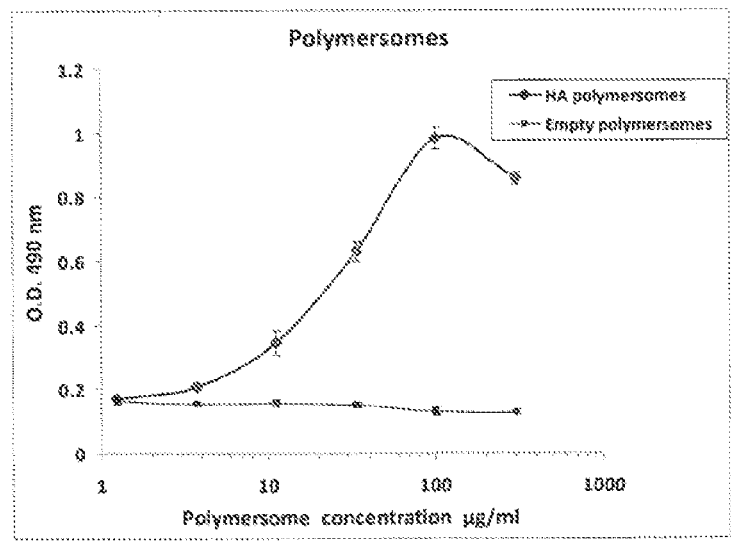
FIG. 6 shows ELISA for HA-inserted and empty (control) polymersomes.
Figure 7:
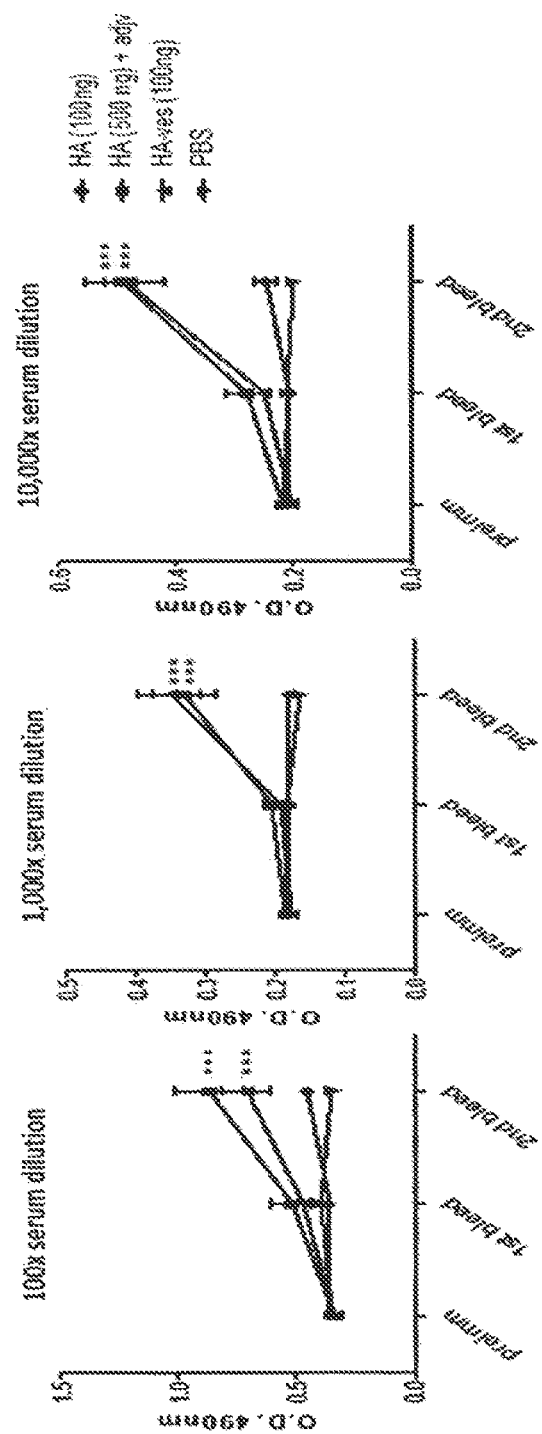
FIG. 7 shows optical density measurements of antibody titers. HA polymersomes (triangles) elicited a higher immune response than free HA (circles) after boost ($2^{nd}$ bleed) at equivalent dose of 100 ng HA (***$p<0.001$ with respect to PBS group). No antibody binding is detected for uncoated wells (data not shown).

To analyse the immunogenicity of alpha-hemolysin presenting polymersomes even further, intradermal injections were carried out. Much attention has been focused on immunization performed in different layers of the skin recently, where subcutaneous and intradermal injections are regaining popularity over intraperitoneal and intramuscular routes because the skin is enriched in antigen-presenting cells such as dendritic cells and macrophages. In addition, a lot of effort has been put into developing easy-to-use needle-free devices that will allow vaccine delivery through the skin. Because of this interest, intradermal injections were carried out in this further experiment. Alpha-hemolysin presenting polymersomes were injected into 3 mice, while free alpha-hemolysin was injected into 2 mice. FIG. 4 shows the immunogenic response of the mice through 3 injections. Interestingly, the alpha-hemolysin presenting polymersomes are now much more efficient than free alpha-hemolysin in eliciting an immune response, where the alpha-hemolysin presenting polymersomes elicited a higher immune response than free alpha-hemolysin in the $2^{nd}$ and $3^{rd}$ bleed. It appears that the immunogenicity of free alpha-hemolysin attenuated by intradermal injection while alpha-hemolysin presenting polymerosomes are still able to generate an immune response. This is probably because the relatively large polymersomes are able to recruit dendritic cells present in the dermis.

In conclusion, the inventors have demonstrated a method of using membrane protein antigen-presenting polymersomes to elicit an immune response by using alpha-hemolysin presenting polymersomes as an example. The alpha-hemolysin presenting polymersomes were able to elicit an immune response more efficiently than both free alpha-hemolysin and alpha-hemolysin injected with an adjuvant. The membrane protein antigen presenting polymersomes can be used for both immunization and antibody production.

Example 2

A method for eliciting in mice an immune response using hemagglutinin-presenting polymersomes is now described in the following paragraphs.

Preparation of Hemagglutinin Polymersomes

The polymersomes were prepared by film rehydration method, BD21 polymer was dissolved in chloroform, and dried as a thin film. Subsequently, ultrapure water was added to rehydrate the film and allow spontaneous formation of polymer vesicles. The resulting vesicle dispersion was then extruded with 0.45 μm and 0.22 μm membranes and dialysed against ultrapure water to remove any remaining solvent. Recombinant Hemagglutinin (HA) Protein (Influenza A Virus H3N2 Wisconsin 67/05, MyBioSource) was supplied as a sterile filtered solution in 10 mM sodium phosphate, pH 7,4,150 M NaCl and 0.005% Tween-20.

The HA polymersomes were formed by adding an aliquot of HA solution to polymer vesicle dispersion. The mixture was then incubated to allow reconstitution HA into the polymersomes. Subsequently, free HA was separated from HA-presenting polymersomes using centrifuge filters. The HA-presenting polymersomes were then resuspended in PBS buffer.

Quantification of HA Concentration

The quantification of the amount of HA inserted nun HA-presenting polymersomes was determined using a standard curve obtained from known concentrations of free HA (FIG. 5). Serial dilutions of free HA, starting at 5 μg/ml and HA polymersomes (FIG. 6) starting at 1:10 dilution in coating buffer (0.1M $CO_3/HCO_3$pH 9-9.8) were coated in a 384-well plate overnight at 4° C. The day after, the wells were washed with PBS and blocked in blocking buffer (1% BSA in 1X PBS, 50 μl/well) at room temperature (RT) for 1 h. Subsequently, anti-HA antibody in blocking buffer was applied, incubated at room temperature (RT) for 1 h and washed with PBS, followed similarly by anti-rabbit HRP-coupled antibodies (1:2.000). Peroxidase activity was quantified through triplicate measurement with OPD substrate. Triplicate measurements were also performed on non-coated wells to determine background signal. Polymersomes without HA inserted were also included as controls to ensure the signal obtained was HA-specific. Extrapolation using the obtained standard curve was performed on the dilutions of HA polymersomes giving rise to signal below saturation, which allowed us to estimate the amount of inserted HA in polymerosomes to be 10.908 μg/ml+/−1.43 (n=3).

Immunization of Mice with HA Polymersomes 100 ng per mouse of HA soluble or in polymersomes were injected subcutaneously in BALB/c mice (3 mice per group) as follows: 1st dose (prime) on day 1 and $2^{nd}$ dose (boost) on day 21. As a positive control, a group of mice was immunized with 500 ng of HA and adjuvant (complete Freund's adjuvant for prime and incomplete Freund's adjuvant for boost, prepared at 1:1 volume ratio according to manufacturer's instruction) while mice were immunized with PBS as negative control. Serum samples were collected before immunization, immediately before the boost and 1 week after boost using capillaries sampling from the mice's cheek.

Quantification of Immune Response 15 ng per well of free HA in coating buffer were coated in a 384-well plate overnight at 4° C. The day after, the wells were washed with PBS and blocked in blocking buffer (1% BSA in 1X PBS) at room temperature (RT) for 1 h. Serum samples of individual mice at each time point was diluted (1:100, 1:1000 or 1:10000) in blocking buffer and incubated on HA-coated or non-coated wells for 1 h at RT (FIG. 7). After 3 washes (PBS 1X), HRP-coupled anti-mouse IgG (1:4000) were incubated for 1 h at RT followed by 3 washes. Peroxidase activity was then quantified with OPD substrate. HA polymersomes elicited a higher antibody response than free HA after boost ($2^{nd}$ bleed) at equivalent dose of 100 ng HA.

Summary

In this example, it has been demonstrated a method of using membrane protein-presenting polymersomes to elicit an immune response by using HA as a model antigen. The HA polymersomes were able to elicit an antibody response more efficiently than free HA at a equivalent immunization dose. The membrane protein antigen-presenting polymersomes can be potentially used for vaccination to induce protective immune responses, as well as for generating antibodies against membrane proteins that are otherwise difficult to induce.

Furthermore, present inventors have used CXCR4 polymersomes to elicit antibodies against CXCR4 to demonstrate the antibodies can be generated for membrane protein antigens that are inserted into the circumferential membrane via in-vitro synthesis.

Hemagglutination inhibition and microneutralization assay with influenza virus (same strain) to test the functionality of the antibodies generated in this work are currently undertaken to prove that they are able to neutralize the virus.

It is also currently being investigated to see if the antibodies raised against CXCR4 polymersomes in this study has much more specific affinity to the CXCR4 antigens produced in cells to demonstrate that this can be used as a tool to generate antibodies against membrane protein antigens.

By "comprising" it is meant including, but not limited to, whatever follows the word "comprising". Thus, use of the term "comprising" indicates that the listed elements are required or mandatory, but that other elements are optional and may or may not be present.

"By consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall he read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

What is claimed is:

1. A method of generating an antibody, comprising administering to a subject a composition comprising a polymersome carrier having a circumferential membrane of an amphiphilic polymer and a non-self immunogen integrated into the circumferential membrane of the amphiphilic polymer of the polymersome carrier, wherein the non-self immunogen is a membrane-associated protein or lipid antigen, wherein the amphiphilic polymer is a poly(butadiene)-poly(ethylene oxide) (PB-PEO) diblock copolymer or a poly(2-methyloxazoline)-b-poly(dimethylsiloxane)-b(2-methyl-oxazoline) (PMOXA-PDMS-PMOXA) triblock copolymer, wherein the membrane-associated protein is selected from the group consisting of a transmembrane protein, G protein-coupled receptor, neurotransmitter receptor, kinase, porin, ABC transporter, ion transporter, acetylcholine receptor, and a cell adhesion receptor.

2. The method of claim 1, further comprising isolating from the subject one or more antibodies generated in response to the administration of the composition comprising the polymersome.

3. The method of claim 1, wherein the PB-PEO diblock copolymer comprises 5-50 blocks PB and 5-50 blocks PEO.

4. The method of claim 2, wherein the subject is a mammalian animal.

* * * * *